United States Patent [19]

Gunderson

[11] Patent Number: 4,934,181

[45] Date of Patent: Jun. 19, 1990

[54] METHOD AND APPARATUS FOR TESTING MATERIALS USING STRAIN AND MOISTURE SORPTION

[75] Inventor: Dennis E. Gunderson, Madison, Wis.

[73] Assignee: The United States of America as represented by the Secretary of Agriculture, Washington, D.C.

[21] Appl. No.: 330,527

[22] Filed: Mar. 30, 1989

[51] Int. Cl.$^5$ .............................................. G01N 19/10
[52] U.S. Cl. ............................................. 73/73; 73/826
[58] Field of Search ................... 73/73, 76, 335, 336, 73/337.5, 337, 865, 826

[56] References Cited

U.S. PATENT DOCUMENTS

| | | |
|---|---|---|
| 1,858,409 | 5/1932 | Mettelsteiner . |
| 2,575,169 | 11/1951 | Green . |
| 2,886,967 | 5/1959 | Conti ................................. 73/73 X |
| 3,016,774 | 1/1962 | Goss ................................. 73/337.5 |
| 3,201,871 | 8/1965 | Ragan et al. ........................ 73/73 X |
| 3,301,057 | 1/1967 | Smith et al. ........................ 73/337 |
| 3,332,281 | 7/1967 | Spangler ........................... 73/159 X |
| 3,546,928 | 12/1970 | Ivarsson . |
| 3,613,437 | 10/1971 | Colgren et al. . |
| 3,733,898 | 5/1973 | Beckford et al. . |
| 3,949,607 | 4/1976 | Nodolf .................................. 73/336 |
| 4,215,568 | 8/1980 | Garber et al. . |
| 4,272,986 | 6/1981 | Lowry et al. . |
| 4,627,293 | 12/1986 | Bechtel ............................. 73/826 X |
| 4,663,969 | 5/1987 | Bibby et al. . |

Primary Examiner—Daniel M. Yasich
Attorney, Agent, or Firm—William J. Connors; John D. Fado; M. Howard Silverstein

[57] ABSTRACT

The invention discloses test methods and apparatus for evaluating the mechano-strain response of various materials, particularly paper and related materials. The moisture sorbed by a specimen is evaluated continuously by observing the change in moisture content of the air in a closed volume surrounding the specimen. The relative humidity of the closed air volume is maintained constant (despite changes in the mass of water vapor in the air) by adjusting the physical volume, and thus the total pressure, of the contained air mass. In a second form, the pressure is adjusted directly. Moisture sorbed by the specimen is calculated from the rise in internal pressure of the closed air mass needed to hold relative humidity constant.

14 Claims, 5 Drawing Sheets

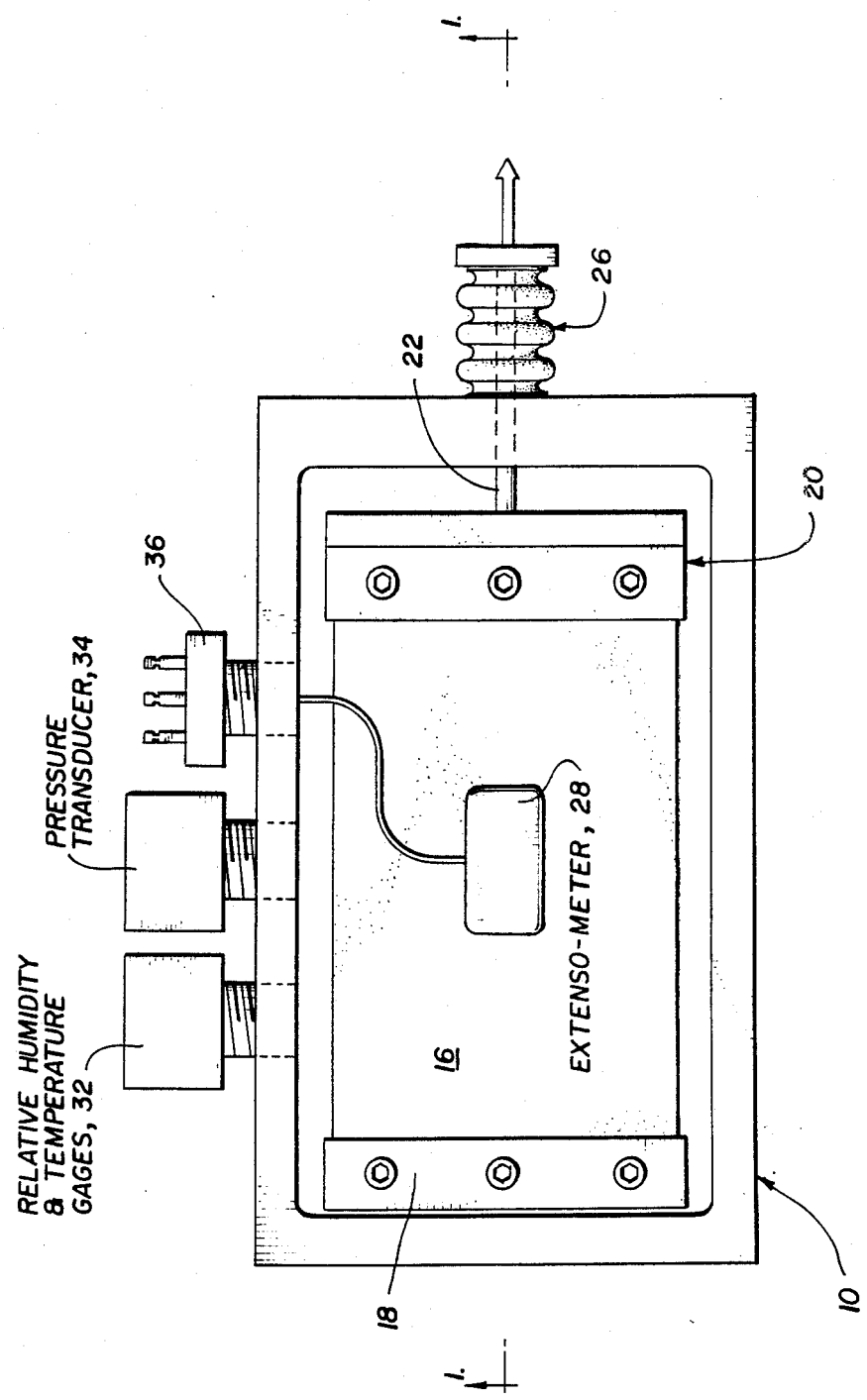

METHOD AND APPARATUS FOR TESTING MATERIALS USING STRAIN AND MOISTURE SORPTION

FIELD OF THE INVENTION

The present invention relates to methods and apparatus for testing materials, in particular, cellulosic and polymer materials. The invention measures the ability of the material to sorb moisture under controlled conditions including the application of strain on the sample. These results are indicative of many other characteristics, parameters, and the like of such materials. The invention relies on the physical principles expressed by the ideal gas law. The apparatus of the invention measures the amount of moisture sorbed by a specimen when strained in a constant relative humidity (RH) and constant temperature environments.

BACKGROUND OF THE INVENTION

It has long been believed that cellulosic and polymer materials sorb moisture in response to applied mechanical stress. W. W. Barkas introduced the concept of elasticity of a gel and calculated the equilibrium between external constraints and the swelling pressure. (Transactions of the Faraday Society 38 (1942)).

In 1962 Kubat and Nyborg of the Swedish Forest Products Laboratory reported that the moisture content of an unbleached kraft paperboard increased from 10.4% to 10.54% when the specimen was loaded to 50% of its tensile strength at a constant 65% relative humidity. They estimated the moisture content gain under load by observing the rate of moisture loss when the load was removed. This approach was necessary because it is not feasible to measure directly the extremely small weight changes which result from the strain in an apparatus which must develop large mechanical force. The Kubat method does not permit direct correlation of sorption with applied load, but did provide a first approximation of the magnitude of the strain-sorption effect. This method is complicated by the interaction of thermodynamic effects. A more sophisticated approach is clearly desirable. The present invention offers the potential for providing unique insight into bonding and functioning of the fiber network in paper and other materials while under stress.

PRIOR ART SEARCH RESULTS

A pre-filing novelty search was performed in the U.S. Patent and Trademark Office, and the following references were developed:

| Patent | Patentee |
|---|---|
| 1,858,409 | E. Mittelsteiner |
| 2,575,169 | H. J. Green, Jr. |
| 3,546,928 | B. W. Ivarsson |
| 3,613,437 | T. Colgren et al |
| 3,733,898 | Bickford et al |
| 4,215,568 | Garber et al |
| 4,272,986 | Lowry et al |
| 4,663,969 | Bibby et al |

None of these references teaches a correlation of changes in volume of a test chamber to relative humidity and the other facets of the invention.

Mittelsteiner 1,858,409 shows changes in barometric pressure inside of an air tight container used for moisture control. The concept of changing the volume of the chamber is not disclosed.

Colgren Pat. No. 3,613,437 shows a rubber bulb 38 which feeds into a closed chamber, a glass bottle 12. However, this bulb is not used as to changes in volume, but merely as an air circulator.

U.S. Pat. No. 4,663,969 to Bibby discloses a device wherein both temperature and humidity are held constant in a plenum containing an aqueous solution and the sample.

Garber U.S. Pat. No. 4,215,568 discloses an apparatus which depends upon maintaining the temperature constant.

Green U.S. Pat. No. 2,575,169 teaches a sealed chamber in which the sample is weighed continuously as the test progresses.

The patents to Ivarsson 3,546,928 and to Lowry 4,272,986 both depend upon changing electrical characteristics of the sample during the test.

Finally, Bickford U.S. Pat. No. 3,733,893 depends upon evaporation rate as it correlates to time to determine certain qualities of a sample.

FEATURES AND ADVANTAGES OF THE INVENTION

Previous and on-going efforts to examine the sorption response of paper and corrugated board in controlled humidity function either by adding or removing moisture from the air or by mixing air sources at different moisture levels to achieve the desired relative humidity. Both methods involve extensive apparatus. Neither allows determination of water sorption quantities in the specimen based on moisture loss in the air volume. Attempts to measure the water sorption quantity in the specimen by direct weighing have been unsuccessful because the weight change in the specimen has been undetectable—obscured by the weight of the load apparatus. The method and apparatus of this invention is an improvement thereover because relative humidity is controlled by altering the pressure of a finite quantity of air and water vapor, and because the water sorbed by the specimen may be determined without weighing or other examination of the specimen itself. Moisture change of the specimen is determined from measurement of the moisture content of the sealed air volume.

SUMMARY OF THE INVENTION

The paper, polymer, and composites industries are all coming to the realization that mechano-sorptive response characteristics of specific materials play a significant role in structural performance. The strain-sorption effect is an essential element of mechano-sorptive response, and it may be the key to understanding the fundamental nature of strain development in complex materials.

As will be clear from the detailed description below, the invention as set forth in the embodiments in the figures is a research tool. However, it is anticipated that the invention will find wide application in various different industries. The invention is applicable not only to paper and related products as specifically described, but to a wide range of non-metallic materials.

In the invention, the moisture sorbed by a specimen is evaluated continuously by observing the change in moisture content of air in a closed volume surrounding the specimen. The relative humidity of the closed air volume is maintained constant (despite changes in the mass of water vapor in the air) by adjusting the volume, and thus total pressure, of the contained air mass. Moisture sorbed by the specimen from the air mass is calculated from the rise in total internal pressure of the closed air mass necessary to maintain a constant relative humidity. The specimen is contained in a sealed chamber of known initial volume. Instruments monitor temperature, relative humidity, internal pressure, and strain of the specimen. Void volume in the chamber is filled with air, containing some water vapor.

The invention provides improved methods and apparatus to accomplish its goals, and does so in a highly efficient and economical manner not heretofore available in the prior art in general.

BRIEF DESCRIPTION OF THE DRAWINGS

FIG. 2 is a plan view of the apparatus of FIG. 1, with the cover removed, and looking generally along the line 2—2 of FIG. 1;

DETAILED DESCRIPTION OF THE PREFERRED EMBODIMENTS

Figure 1:
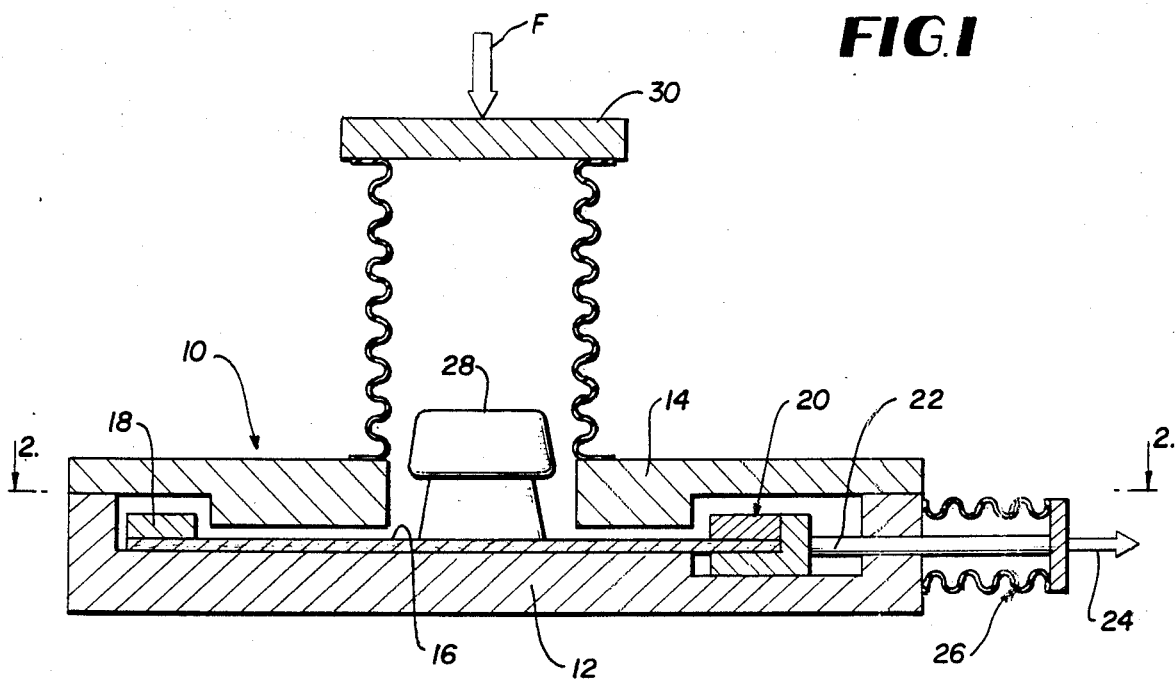
FIG. 1 shows a first embodiment of apparatus embodying the invention, the view being taken on line 1—1 of FIG. 2.

FIGS. 1 and 2 show a first embodiment of a test cell 10 in accordance with the invention. Cell 10 is made up of a base member 12 and a top member 14 removably secured thereto in an air tight manner by means not shown. A specimen 16, which may be a piece of kraft paper, fiberboard, or other non-metallic material, is held in the air tight space within the cell 10 by a fixed clamp 18 at one end thereof, and by a movable clamp assembly 20 at the other end thereof. A rod 22 is fixed to the movable clamp 20. Arrow 24 indicates a load L applied to the rod externally of the cell 10 to thus apply tensile force to the specimen 16. Bellows assembly 26 assures the air tight character of the space within the cell 10 while permitting motion of the rod 22. A device 28, known as an "extenso-meter" is provided on the specimen 16 to measure the elongation or deformation of the specimen 16 during the testing procedure.

Of course, as is clear, the purpose of the load L acting through the rod 22 is to provide a controlled stress to cause strain in the sample 16, and to do so in such a way that there is no entry of air, change in pressure, or the like in the space inside the cell 10, in accordance with the invention.

Means are provided to control the total air space or volume inside the test cell 10. To this end a force F is applied to the bellows assembly 10, the bellows compresses and causes the internal pressure to rise. As testing proceeds, appropriate changes in force F, which will change into appropriate changes in the internal pressure inside cell 10, can be accomplished in accordance with the invention.

Means are provided to measure the relative humidity, the temperature, the pressure, and to operate the meter 28. In addition, means are provided to supply electrical energy to those parts of the apparatus as required. To this end, block 32 indicates the relative humidity (RH) and temperature gauges; block 34 indicates a pressure transducer, gauge or the like; and the schematic illustration 36 represents an electrical connector and feeding device for the meter 28 and other parts of the apparatus as may require electrical energy, not shown. All three of the blocks 32, 34 and 36 communicate with the space occupied by the specimen 16 inside the cell 10 in an air tight manner.

Figure 3:
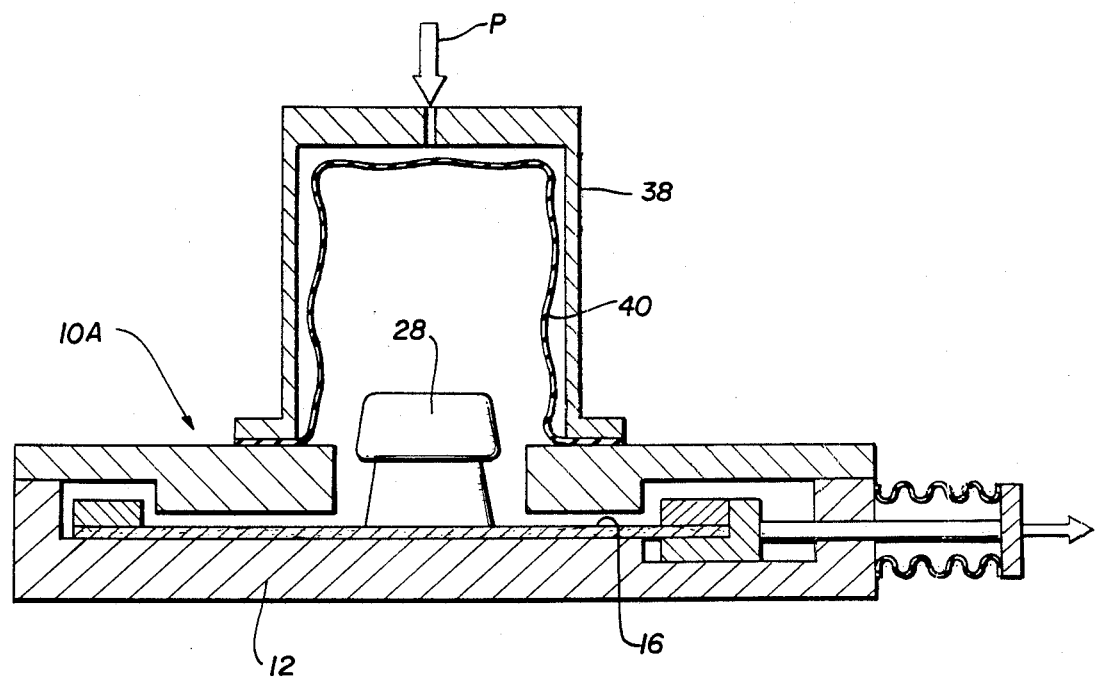
FIG. 3 is a view similar to FIG. 1 illustrating a second embodiment of the invention.

FIG. 3 shows an alternative embodiment of the invention wherein similar parts are indicated by the identical reference numerals used above. Basically, the FIG. 3 embodiment differs from the FIGS. 1 and 2 embodiment in that the air space inside the cell 10 is controlled by a pneumatic or other pressure force P rather than by a physical force F.

More specifically, the cell 10A replaces the bellows assembly 30 of cell 10 with a housing 38 which contains an impermeable membrane or bladder 40. In this manner, the fluid used to create pressure P is isolated from the air and moisture inside the test cell 10A. Changes in pressure P cause corresponding contractions or expansions of bladder 40, to thus in turn control the pressure in the space inside the cell 10A. By using a bladder 40 which is relatively flexible and easily deformed, the apparatus 10A can be arranged so that the interior pressure will be essentially equal to pressure P. This greatly facilitates use of the invention in the form of the apparatus of FIG. 3.

Thus, FIG. 3 provides improved and simplified control of the pressure inside the cell 10A acting on the specimen 16, while at the same time preventing any exchange of air or moisture into or out of that internal space. If desired, servo means or the like can be provided to achieve a constant internal relative humidity, using the blocks 32, 34 and 36 of FIG. 3 (which will of course also be present in the FIG. 3 form). This can be done in conjunction with computer means or other automatic control means to achieve that desirable goal, i.e., an automatic constant internal relative humidity.

THEORY AND OPERATION OF THE INVENTION

For an ideal gas, the total pressure in the sealed chamber ($P_T$) is the sum of vapor partial pressure ($P_v$) and dry air partial pressure ($P_a$). Relative humidity RH is, by definition, the ratio of vapor partial pressure ($P_v$) to the saturation pressure ($P_g$) of water vapor at the ambient temperature. When a tensile load (L) is applied to the specimen by external means through the movable clamp assembly 20, water vapor will be sorbed from the sealed volume into the specimen; and vapor partial pressure ($P_v$) in the sealed volume will tend to decrease. In order that $P_v$ and relative humidity will be constant, a pressuring force (F) is applied to the bellows 30. The force applied is continually controlled so as to maintain RH (monitored by RH and temperature gauges in block 32) constant. This force increases the total internal pressure $P_T$ and maintains $P_v$ at a constant level despite the fact that some water vapor has been sorbed into the specimen.

In the FIG. 3 form, ($P_T$) corresponds substantially exactly to external pressure P.

Temperature is maintained constant by means of free heat exchange from the cell to the environment, so that the temperature in the cell is maintained at ambient temperature by natural equilibrium of the test cell to the ambient air.

From the theoretical development below, it is clear that the mass of water vapor sorbed into the specimen can be calculated from the observed change in $P_T$ monitored by the pressure transducer 34.

In summary, the moisture gain of the specimen exposed to external stress, at constant temperature, in a constant relative humidity atmosphere can be evaluated on a continuous basis without direct measurement of specimen weight. Thus, an otherwise extremely difficult, if not practically impossible, measurement is reduced to simple monitoring and adjustment of total internal pressure. In the data shown in FIGS. 4-6 and described below, moisture changes in tenths of milligrams while the specimen is subject to loads in excess of 30 KG were measured.

Normal ranges of operation for work done with the invention are:
Temperature: −20° F. to 150° F.
Pressure: 0 to 30 psi gauge
Relative humidity: 0 to 100%

Figure 4:
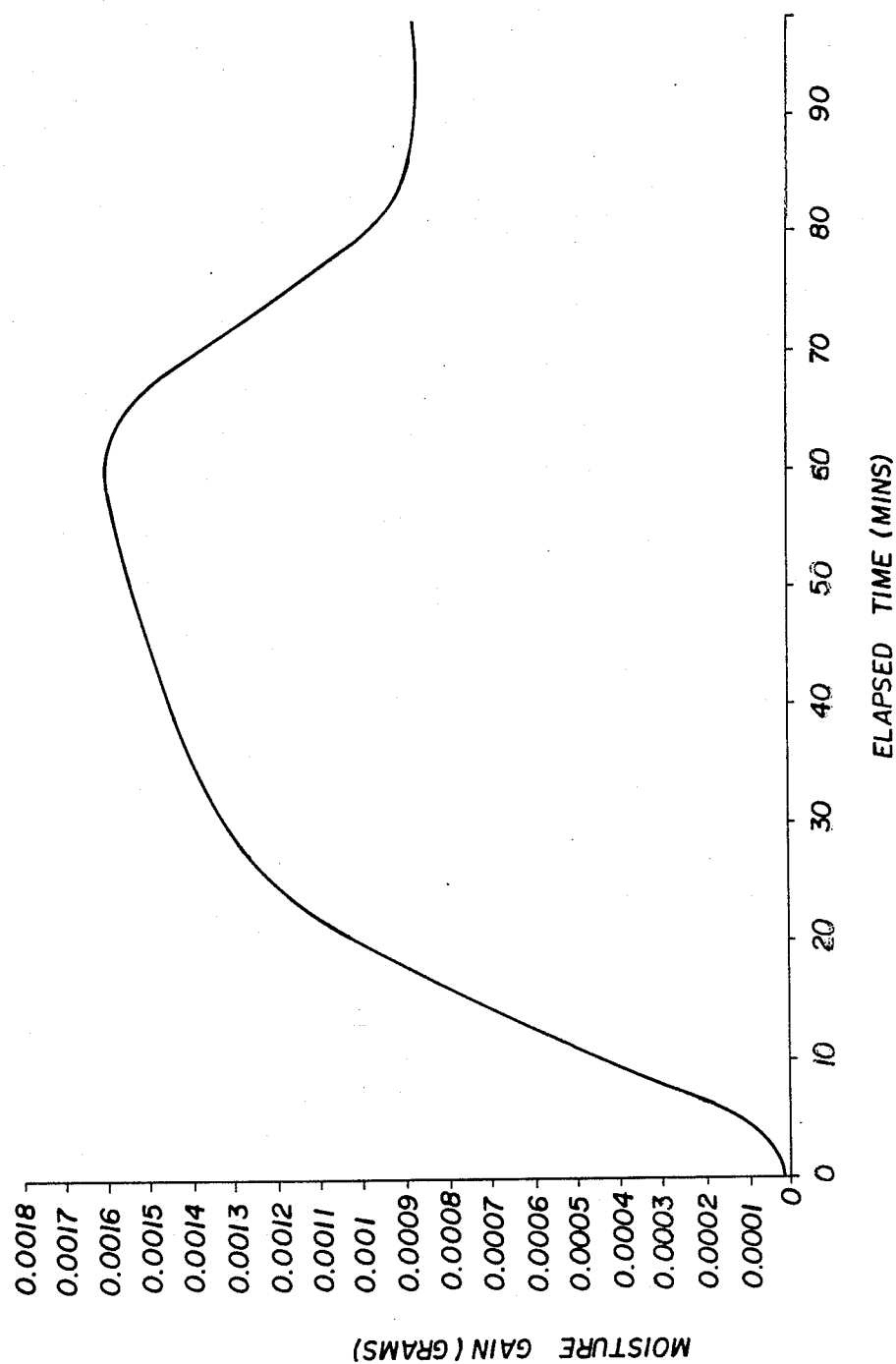
FIGS. 4, 5 and 6 are curves illustrating the performance of the method and apparatus of the invention.
Figure 5:
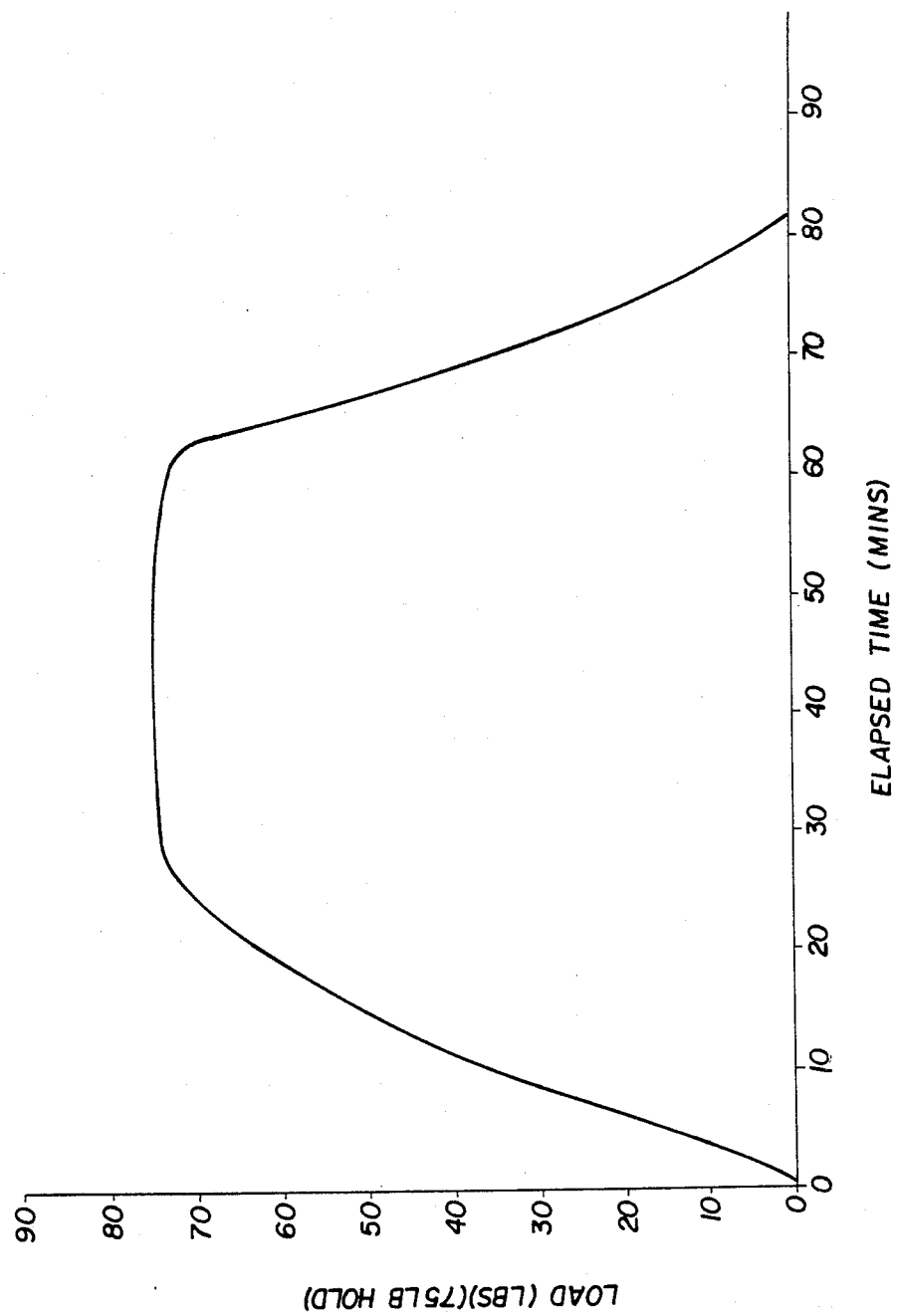
Figure 6:
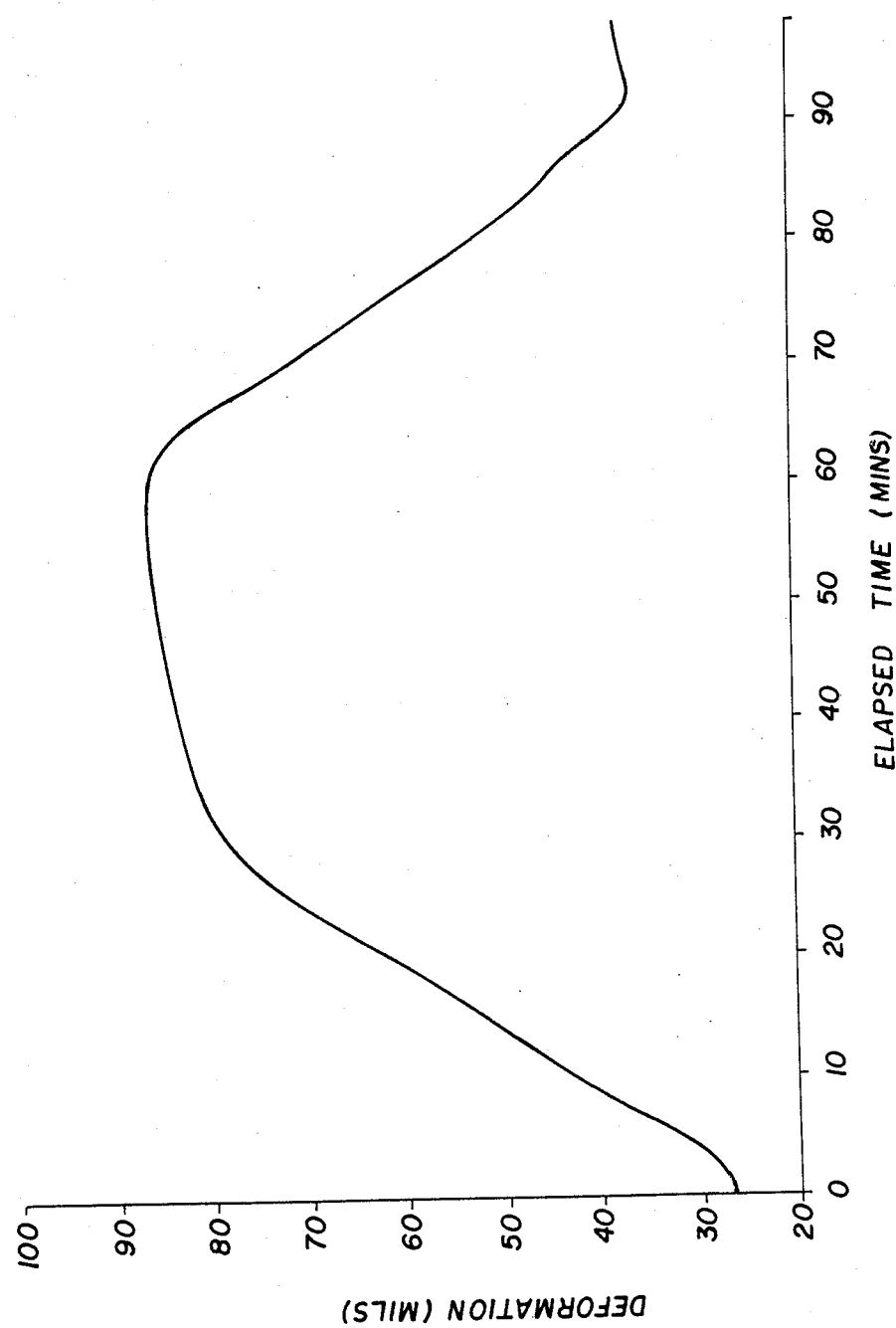

FIGS. 4, 5, and 6 represent actual experimental results obtained with the apparatus. A dry specimen of kraft paper measuring 4"×6" and weighing 3.2 grams was placed in the apparatus. Prior to closing and sealing the apparatus, the interior was equilibrated to 24° C. and 48% relative humidity. The apparatus was then closed and sealed. Temperature and humidity were held constant throughout the subsequent strain sorption test. FIG. 5 shows the load which was applied to the 4-inch width of the specimen. Load was gradually increased during the first 30 minutes of the test cycle to a maximum of 75 lb. Load was held constant for the next 30 minutes and then gradually reduced to 0 load. During this time, chamber volume is adjusted by means of the bellows to maintain relative humidity constant at 48%.

FIG. 6 shows the deformation (extension) of the specimen which takes place due to the application of load. During the first 30 minutes, the deformation increases in almost direct proportion to the applied load. From 30 minutes to 60 minutes, deformation increases even though the load is held constant. This behavior is commonly referred to as creep deformation under constant load. From 60 minutes to 80 minutes, deformation is reduced, again almost in direct proportion to the progressive reduction in load. From 80–90 minutes, deformation continues to decrease even though the load is constant to 0. This behavior is known as stress relaxation. FIG. 4 shows the moisture gained (sorbed) by the specimen during the test as calculated according to the method taught by this invention. The specimen clearly sorbs moisture as deformation increases and loses moisture when deformation decreases. The method is easily capable of resolving moisture changes as small as 0.00005 gram even while the specimen is under load of 75 lb (34,000 grams). This would not be possible with methods which attempt to measure weight change directly.

Note that this specimen, which as been equilibrated to test conditions from dry conditions, experienced a net gain in moisture as a result of the load-relax experience. Specimens equilibrated to test conditions from a high humidity state demonstrates similar response but with a net loss of moisture in the same load cycle. It is believed that this is the first time that this previously only hypothesized behavior has been experimentally observed and quantified.

The following mathematical analysis describes how moisture change in the specimen 16 is determined from measurements of total pressure of the air and moisture mixture sealed inside the space within the invention test cell 10 or 10A.

o—O—o

DEFINITIONS OF TERMS

W = Mass of water vapor sorbed by the specimen due to strain resulting from applied tensile load
M = Mass of water vapor in the specimen
$m_v$ = Mass of water vapor in the closed volume surrounding the specimen
P = Pressure of an ideal gas
$P_a$ = Partial pressure of dry air component in air-water vapor mixture
$P_g$ = Saturation pressure of water vapor at a specified temperature
RH = Relative humidity of air in closed volume surrounding the specimen
$P_T$ = Total pressure of air/water vapor mixture inside test cell
$P_v$ = Partial pressure of gaseous water vapor component in an air-water vapor mixture
R = Universal gas constant
T = Absolute temperature of the apparatus
$V_1$ = Initial volume of the closed chamber
$V_2$ = Volume of the chamber as adjusted to maintain constant relative humidity during straining In the following formulas, with regard to the terms M, $m_v$, $P_a$, $P_T$, and $P_v$, the additional inclusion of subscript 1 denotes the initial state in which no load is applied to the specimen; and the additional inclusion of subscript 2 denotes a state in which the specimen is strained due to application of tensile load, and chamber volume is adjusted to maintain constant relative humidity.

MATHEMATICAL ANALYSIS

Total water content before straining of specimen = Total water content in strained condition $$M_1 + m_{v1} = M_2 + m_{v2}$$

If relative humidity is controlled at a constant level as the specimen is strained, then moisture sorbed by the specimen is:

$$W = M_2 - M_1 = m_{v1} - m_{v2} \quad (1)$$

One can represent $m_v$ in terms of pressure and temperature from the ideal gas law:

$$m_v = \frac{PV}{RT} \quad (2)$$

Substituting (2) into (1)

$$W = \frac{P_{v1}V_1}{RT} - \frac{P_{v2}V_2}{RT} \quad (3)$$

Relative humidity is by definition:

$$RH = \frac{P_v}{P_g} \text{ and } P_v = RHP_g$$

Because temperature is constant in use of the invention, $P_g$ is also constant.

$$P_{v2} = P_{v1} \quad (4)$$

-continued
$$W = \frac{P_{v1}}{RT(V_1 - V_2)}$$

From equation (4), it is apparent that the moisture sorbed by the specimen can be calculated from knowledge of the initial partial pressure of water vapor in the system ($P_{v1}$) and the chamber volume.

However, because it is not convenient to measure $V_2$ accurately during the test, it would be more useful to represent W in terms of $V_1$ and the total pressures $P_{T1}$ and $P_{T2}$.

According to the Dalton model for partial pressures of gas mixtures:

$$P_T = P_v + P_a$$

Accordingly:

$$P_{T1} = P_{v1} + P_{a1} \quad (5)$$

(normally 14.7 psia)

$$P_{T2} = P_{v2} + P_{a2} \quad (6)$$

$P_{a2}$ and $P_{T2}$ will vary with changes in volume of the closed system. If we substitute $P_{v1}$ for $P_{v2}$ in (6), $$P_{T2} = P_{v1} + P_{a2} \quad (7)$$

We know from the ideal gas law that:

$$P_{a1} V_1 = P_{a2} V_2$$

Solving for $P_{a2}$ $$P_{a2} = \frac{P_{a1} V_1}{V_2} \quad (8)$$

Substituting (8) into (7)

$$P_{T2} = P_{v1} + \frac{P_{a1} V_1}{V_2} \quad (9)$$

Rearranging (5)

$$P_{a1} = P_{T1} - P_{v1} \quad (10)$$

Substituting (10) into (9)

$$P_{T2} = P_{v1} + \frac{V_1}{V_2} (P_{T1} - P_{v1})$$

Solving for $V_2$ $$V_2 = \frac{V_1(P_{T1} - P_{v1})}{(P_{T2} - P_{v1})} \quad (11)$$

Substituting (11) into (4)

$$W = \frac{P_{v1}}{RT} \left( V_1 - \frac{V_1(P_{T1} - P_{v1})}{(P_{T2} - P_{v1})} \right)$$

and simplifying:

$$W = \frac{P_{v1} V_1}{RT} \left( 1 - \frac{P_{T1} - P_{v1}}{P_{T2} - P_{v1}} \right) \quad (12)$$

Thus, the moisture gain of the specimen is calculated from knowledge of the initial conditions and total pressure readings observed during the experiment.

o—O—o

While the invention has been described in considerable detail above, it is to be understood that this detailed description is by way of example only, and the protection granted is to be limited only within the spirit of the invention and the scope of the following claims.

What is claimed is:

1. A method of determining the mechano-sorptive response characteristics of a specimen by measuring the strain-sorption effect in said specimen, comprising the steps of providing a test cell, said test cell defining a sealed internal space, mounting said specimen within said space, applying a predetermined load to said specimen to thereby induce a predetermined strain in said specimen, measuring the relative humidity within said space, measuring the pressure within said space, maintaining said relative humidity substantially constant while said strain is being induced in said specimen, and performing said last mentioned maintaining step by the step of varying the pressure within said space.

2. The method of claim 1, and the steps of filling said space with ambient air, and maintaining the temperature in said cell at ambient temperature by natural equilibrium of said test cell to the ambient air.

3. The method of claim 1, and performing said last mentioned varying pressure step by the step of varying the volume of said space, performing said varying volume step by applying a force to bellows means, and arranging said bellows means as part of said test cell so that said bellows means defines the size of said space.

4. The method of claim 1, and performing said last mentioned varying pressure step by the step of varying the volume of said space, performing said varying volume step by applying a pressure to flexible bladder means, and arranging said bladder means as part of said test cell so that said bladder means defines the size of said space, whereby said pressure applied to said bladder means is substantially equal to the pressure in said space.

5. The method of claim 1, and performing the method at an operating temperature in the range of about $-20°$ F. to about $150°$ F.

6. The method of claim 1, and performing the method at an operating pressure in the range of about 0 to about 30 psi gage.

7. The method of claim 1, and performing the method at a relative humidity in the entire range up to 100%.

8. The method of claim 1, and the step of applying said predetermined load to said specimen from outside said test cell.

9. Apparatus for determining the mechano-sorptive response characteristics of a specimen by measuring the strain-sorption effect in said specimen, comprising a test cell, said test cell including means defining a sealed internal space, means for mounting said specimen within said space, means for applying a predetermined load to said specimen to thereby induce a predetermined strain in said specimen, means for measuring the relative humidity within said space, means for measuring the pressure within said space, means for maintaining said relative humidity substantially constant while said strain is being induced in means for specimen, and said last mentioned maintaining means including means for varying the pressure within said space.

10. The apparatus of claim 9, means for filling said space with ambient air, and means for maintaining the temperature in said cell at ambient temperature by permitting natural temperature equilibrium to occur between said test cell including said space and the ambient air.

11. The apparatus of claim 9, and said last mentioned varying pressure means comprising means for varying the volume of said space, said varying volume means comprising bellows means, and means for arranging said bellows means as part of said test cell so that said bellows means defines the size of said space.

12. The apparatus of claim 9, and said last mentioned varying pressure means comprising means for varying the volume of said space, said varying volume means comprising flexible bladder means, and means for arranging said bladder means as part of said test cell so that said bladder means defines the size of said space, whereby a pressure applied to said bladder means is substantially equal to the pressure in said space.

13. The apparatus of claim 9, and means for applying said predetermined load to said specimen from outside said test cell.

14. The apparatus of claim 13, said load applying means comprising an arrangement of a first specimen holding clamp fixed to said cell inside said space, a second specimen holding clamp inside said space arranged for movement in response to said load and deformation of said specimen, rod means extending from second clamp through a portion of said all, and means to seal the region where said rod extends out of said cell in air tight manner.

* * * * *